United States Patent [19]

Dotson et al.

[11] Patent Number: 4,464,338

[45] Date of Patent: Aug. 7, 1984

[54] IN SITU TRITIUM BOREHOLE PROBE FOR MEASUREMENT OF TRITIUM

[75] Inventors: Danny W. Dotson, Sterling Park, Va.; Jon L. Mikesell, Greenbelt; Frank E. Senftle, Chevy Chase, both of Md.

[73] Assignee: The United States of America as represented by the Secretary of the Interior, Washington, D.C.

[21] Appl. No.: 200,110

[22] Filed: Oct. 24, 1980

[51] Int. Cl.$^3$ .................................... G01N 31/00
[52] U.S. Cl. .................................... 422/78; 250/303; 250/432 R; 422/68; 436/39; 436/57
[58] Field of Search ............... 422/68, 71, 78; 436/28, 436/57, 58, 59, 39; 250/253, 255, 256, 308, 260, 303, 356.2, 432 R

[56] References Cited

U.S. PATENT DOCUMENTS

| | | | |
|---|---|---|---|
| 2,888,569 | 5/1959 | Jones | 250/260 |
| 3,226,197 | 12/1965 | Lewis | 250/303 |
| 3,248,540 | 4/1966 | Youmans | 250/260 |
| 3,655,982 | 4/1972 | Gelezunas | 250/432 R |
| 4,267,446 | 5/1981 | Brown et al. | 250/255 |
| 4,294,798 | 10/1981 | Capuano et al. | 422/68 |

FOREIGN PATENT DOCUMENTS 69391 6/1977 Japan .................................... 422/68

OTHER PUBLICATIONS

"Tritium Tracing—A Rediscovery", Nucleonics, May 1958, pp. 62-67.

Tamers, "Benzene Method Tritium in Rain Without Isotope Enrichment", Nucleonics, Jun. 1963, pp. 90-94.
Jalbert, "A Monitor for Tritium in Air Containing Other Beta Emitters", Proc. 23rd Conf. Remote Sys. Tech., San Francisco, Nov. 17-20, 1975, pp. 89-93.

Primary Examiner—Alfred E. Smith
Assistant Examiner—Carolyn E. Fields
Attorney, Agent, or Firm—Thomas Zack

[57] ABSTRACT

An apparatus for measuring the in situ levels of tritium in ground water at depth in the earth. A tritium analyzer is made to fit in a sonde or probe which is placed in a borehole. This analyzer can perform a programmed cycle and has a sample intake to allow ambient water to enter; a reaction chamber; a drying chamber; an ion chamber; a cryogenic gas pump, and a spent capsule collection chamber. After the water sample is brought into the unit, it rises into the reaction chamber where it reacts with a preweighed quantity of calcium carbide in a capsule to yield acetylene. Next the acetylene vapor passes through the drying chamber to remove excess water and then flows into the evacuated ion chamber. Following this, the ion chamber is sealed off and a count of tritium beta decay events is started. Following the completion of the count, a valve is opened to remove the acetylene from the ion chamber with the cryogenic gas pump. The spent capsule containing the residue from the reaction is ejected into a collection chamber. Last, the holder for the preweighed calcium carbide capsule is refilled from a stock of such capsules in preparation for a new measurement cycle.

3 Claims, 1 Drawing Figure

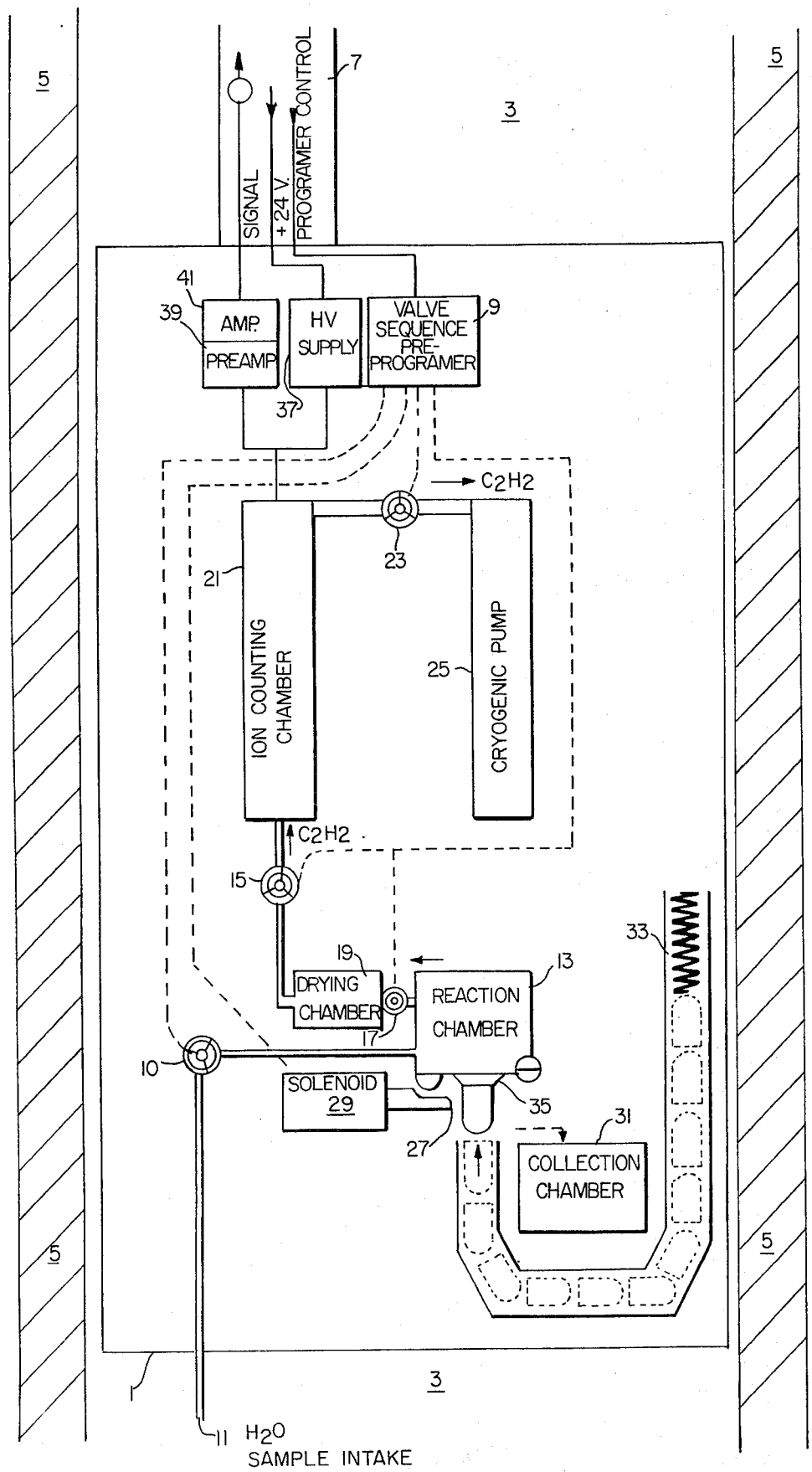

IN SITU TRITIUM BOREHOLE PROBE FOR MEASUREMENT OF TRITIUM

BACKGROUND OF THE INVENTION (1) Field of the Invention

Our invention is a borehole probe used for measuring the tritium concentration in ground water.

(2) Description of the Prior Art

One of the radioactive waste products from nuclear power production is tritium or radioactive hydrogen of mass number 3. The release of radioactive waste products into rivers and streams introduces this tritium into the environment. Public and private agencies involved with nuclear regulation, the protection of the enivornment, and the study of water resources are concerned with the levels of tritium in our water supply. Presently, the technique for determining tritium levels in water is performed in the laboratory by first purifying the sample of obtained water and then releasing the tritium by electrolysis. Another technique employs calcium carbide to generate acetylene gas from the water sample. Our presently disclosed invention makes the separation of the sample site and incorporates the water purification previously done into one process.

Many devices are described in the prior art to detect the presence of radioactive isotopes including beta particle emitters such as tritium. These include liquid scintillation systems and gas proportional counters. In the gas proportional counter system, a voltage is applied across a chamber containing a special gas mixture that incorporates the tritium. Pulses of current which occur as the gas undergoes radioactive decay and ionization are counted to yield the desired result. The U.S. Pat. No. 2,470,221 (A. Scherbatskoy) discloses an ionization chamber system used in a borehole to detect radiations from radioactive materials in subsurface strata. Ions produced in the space 49 due to radiation entering the ionization chamber 30 will be detected at the alternating electric field (column 5, lines 58 et seq.). Such a system would be applicable to the measuring of natural gamma ray radiation coming from the rock surrounding the borehole because gamma rays can penetrate through the rock and the sonde casing. Tritium emits weak beta particles which could not penetrate such a casing. Our invention is sensitive only to these relatively low energy beta particles (0.026 million electron volts or MeV). Gamma rays are more easily detected by the Scherbatskoy device because of their high penetrating power and generally high energy (0.001 to 3 MeV) levels.

Deuterium has been used as an isotope tracer to measure the flow of ground water (U.S. Pat. No. 3,291,997, E. L. Albenesius et al). Deuterium, like tritium, is an isotope of hydrogen. However, unlike tritium, it is not radioactive. It is interesting to note that this inventor (see column 1, lines 40–43) thought that the weak radiation from tritium made it "essentially impossible to detect in situ."

None of the known prior art discloses systems that are capable of measuring the tritium content of water in situ as disclosed herein. U.S. Pat. No. 3,506,402 (H. F. Simon) discloses a technique for the analysis of organic compounds which can be marked or labeled with either radioactive carbon ($^{14}C$) or tritium ($^3H$). To accomplish its purpose, the organic compounds are broken up by a catalyst into compounds that do not condense on the walls of the ionization chamber. Methane gas is used as a carrier gas and the ionization chamber is a flow-through type. In our invention, the water is converted to a non-condensing material (acetylene) which acts as a carrier gas for the tritiated acetylene. We do not use a flowing gas in the ionization chamber as in Simon but instead use a fixed amount of gas which is introduced into the evacuated ionization chamber. The use of bulky apparatus such as that disclosed in Simon would be impractical in a borehole.

One previous patent which could be used to measure beta radiation in a borehole is disclosed in the S. B. Jones patent (U.S. Pat. No. 2,857,522). However, unless the tritium were present in very large concentrations, the phosphor (10) beta detector of Jones would be unsuitable. The metal or quartz protective window used by Jones would attenuate virtually all of the natural beta radiation striking it. Because the beta radiation emitted by tritium is so low in energy, it would be even more generally attenuated before reaching the phosphor. In contrast to the Jones patent, which is sensitive only to very high beta emitters, our invention is sensitive to very low concentrations. This is because the tritium is introduced directly into the counting chamber and hence the radiation experiences no attenuation.

What we have provided in our invention is an in situ low level tritium counting device which operates automatically to change water samples in the borehole, to eject the previous sample, and to insure the total program evaluation sequence.

SUMMARY OF THE INVENTION

The in situ tritium analyzer forming the subject matter of this disclosure is housed in a probe (sonde) adapted to fit into a borehole. The basic components of the analyzer include: a sample intake; a dispenser of preweighed capsules of calcium carbide; a reaction chamber; a drying chamber; an ion chamber; a cryogenic gas pump, and a collection chamber. When in the borehole, a device actuated at the surface causes these components to begin a programmed cycle of operation which starts with the introduction of a given quantity of a water sample at the intake. Next, this water reacts in the reaction chamber with a preweighed quantity of calcium carbide to form a non-condensing gas ($C_2H_2$) which is passed through the drying chamber to the ion chamber. The ion chamber is sealed off and a beta particle count is performed. After the counting period, the cryogenic gas pump removes the gas containing the tritium from the ion chamber by absorbing it onto a getter material within the pump. The chamber is left in an evacuated state in preparation for the next sample. Finally, the spent capsule containing the residue of the calcium carbide reaction drops into a collection chamber and the tritium analyzer is ready to accept a new water sample.

The primary object of this invention is to provide an improved in situ system for measuring tritium levels in water at depth in a borehole.

DESCRIPTION OF THE DRAWINGS

The FIGURE depicts a block diagram of the preferred embodiment of the system shown in situ in a borehole.

One of the principal problems encountered in making tritium measurements in situ concerns differentiating between beta counts from tritium and counts from other natural beta particles in the water sample. To eliminate the natural beta emitters in the water, we have removed the hydrogen (and hence the tritium), from the water by converting it to acetylene ($C_2H_2$). The water sample and whatever tritium atoms may happen to be in it are converted to acetylene gas ($C_2H_2$) by mixing it with a preweighed quantity of calcium carbide ($CaC_2$) according to the reaction:

$$CaC_2 + 2H_2O \rightarrow C_2H_2 + Ca(OH)_2 \qquad (1)$$

The FIGURE shows a block diagram of how the basic apparatus would be mounted in a probe or sonde housing 1 that has been lowered into a predrilled borehole 3 of the surrounding earth 5. Cable 7 to the surface serves the dual function of vertically supporting the probe and providing an electrical connection to its instruments. Initially a signal from the surface via cable 7 signals a valve sequence programmer 9 such as Model No. 22-211-313 made by the Cole Instrument Corp. to begin a program which goes through the following cycle. A valve 10 in the sample intake unit 11 is activated by the programmer to let in a given quantity of water. This water then rises into the reaction chamber 13 where it reacts with a preweighed quantity of calcium carbide in accordance with equation (1) to yield acetylene gas. Next, valves 15 and 17 allow the acetylene gas to pass through a water vapor drying chamber 19 to prevent the condensation of water in the counting chamber. Following this, the acetylene moves into the ion chamber 21. The ion chamber is then sealed off from the reaction chamber and a count of the beta decay events is started. One type of ion chamber which could be used for this purpose is Model GCIK may by the Nuclear Development Lab. Inc. of Kansas City, Mo. During the predetermined counting time, electrical pulses corresponding to the tritium beta decay events detected are sent via cable 7 to conventional data collection equipment at the surface such as the Tenelec Corp. counter-scaler, Model 264. A valve 23 is then opened to the cryogenic gas pump 25, i.e., a cryogenic absorption-type pump cooled with solid argon. This removes the acetylene from the ion chamber to the getter within the pump. After the pumping cycle is completed, the ion chamber is automatically sealed and readied for the next sample of acetylene. Simultaneous with the count of beta particles from the acetylene sample, the capsule 27 which held the calcium carbide is ejected from the bottom of the reaction chamber by a solenoid 29 and the capsule, with the residue of the chemical reaction drops into the collection chamber 31. A fresh capsule of the preweighed calcium carbide from the spring-loaded capsule delivery tube 33 is joined to the reaction chamber via hermetic seal 35 for use with the next water sample. Approximately twenty-five samples of underground water can be analyzed for tritium with this embodiment of the invention before reloading of the calcium carbide sample supply 33 is necessary.

Also illustrated in the FIGURE are the dotted lines from the sequencer 9 to the valves and solenoids it controls, the conventional unit high voltage power supply 37, the preamplifier 39, and the amplifier 41. One example of a high voltage power supply which could be used is Model Q-30 "Minaturized Hi-Voltage Supply" built by Vensus Scientific, Inc. The preamplifier and amplifier units shown could be model numbers A-203–A-206 built by the Amptek Inc. company. Other (not shown) functioning units on the earth's surface which interreact via cable 7 with the illustrated systems include a winch to raise/lower the sonde and its contents made by the Widco Corp.; the mentioned counter-scaler, Model 264, made by the Tenelec to receive and output a visual ditial display of the number of beta counts, and a, connected to unit 37, twenty-four volt, 10 ampere power supply built by the Lambda Electronics Company.

It is apparent that many changes can be made to the materials, design, and other variables for the preferred embodiment. None of these changes should be used to limit the scope and extent of the invention which is to be measured only by the claims that follow:

We claim:

1. A system for determining the in situ activity of tritium in water by measuring the beta particles emitted by the tritium, comprising within a common sonde housing capable of being used in a borehole:
   means for obtaining an in situ predetermined quantity sample of the water under test;
   a reaction chamber means for sequentially receiving one at a time chemically reactive preweighed material units which will react with the water sample and convert the hydrogen and tritium therein into a gas sample;
   an ion chamber for receiving the converted gas sample from the reaction chamber, said chamber being sealed after the receipt of the sample;
   means for measuring the beta count emitted from the gas sample while in said sealed ion chamber;
   means for evacuating the gas sample from the ion chamber after the count has been completed and allowing the introduction of a new gas sample thereinto;
   means for supplying the preweighed material units to the reaction chamber to mix with a different in situ water sample; and
   a collection chamber to receive the residue from the material units after reacting with the water.

2. The system of claim 1 wherein the system has additional means for preprogramming its operation for: obtaining in the in situ water samples and sending them individually to the reaction chamber, supplying the preweighed units to the reaction chamber to react therewith with the water samples, receiving the gas sample in the ion chamber, measuring the beta count for each gas sample, removing the gas sample from the ion chamber, and for then setting up the system for allowing the repeating of the foregoing five step operation.

3. The system of claim 1 wherein the chemically reactive preweighed material received in said reaction chamber means which reacts with the water sample is calcium carbide and reacts according to the reaction:

$$CaC_2 + 2H_2O \rightarrow C_2H_2 + Ca(OH)_2.$$

* * * * *